US005482053A

United States Patent [19]
Kelly

[11] Patent Number: 5,482,053
[45] Date of Patent: Jan. 9, 1996

[54] CONDOM LUBRICANTS CONTAINING ZINC AS AN ANTI-VIRAL AGENT

[76] Inventor: Patrick D. Kelly, 33 Berry Oaks, St. Louis, Mo. 63122

[21] Appl. No.: 57,001

[22] Filed: May 3, 1993

Related U.S. Application Data

[63] Continuation-in-part of Ser. No. 737,169, Jul. 29, 1991, Pat. No. 5,208,031, and a continuation-in-part of Ser. No. 528,495, May 25, 1990, abandoned, which is a continuation-in-part of Ser. No. 362,058, Jun. 6, 1989, abandoned.

[51] Int. Cl.$^6$ .................................................. A61F 6/04
[52] U.S. Cl. .................................... 128/844; 128/918
[58] Field of Search .................................... 128/842, 844, 128/918; 604/330, 347–353

[56] References Cited

U.S. PATENT DOCUMENTS

| 3,136,417 | 6/1964 | Clinch | 128/844 |
|---|---|---|---|
| 4,407,818 | 10/1983 | Lionelle | 424/289 |
| 4,465,666 | 8/1984 | Lukas | 424/145 |
| 4,684,490 | 8/1987 | Taller | 128/844 |
| 4,869,270 | 9/1989 | Ueno | 128/844 |
| 4,992,259 | 2/1991 | Schiraldi | 424/49 |
| 5,165,953 | 11/1992 | Shlenker | 128/844 |
| 5,208,031 | 5/1993 | Kelly | 424/412 |

FOREIGN PATENT DOCUMENTS

WO87/02246  4/1987  WIPO ................ A61K 33/24

OTHER PUBLICATIONS

Merck Index, pp. 1598–1601, Eleventh edition (1989).
Eby, G. A., and W. W. Halcomb, "Use of topical zinc to prevent recurrent herpes simplex infection: review of literature and suggested protocols," *Medical Hypotheses* 17: 157–165 (1985).
Sergio, W., "Zinc Salts that may be Effective Against the Aids Virus HIV," *Medical Hypotheses* 26(4): 251–253 (1988).
Chvapil M., et al., "Preliminary testing of the contraceptive collagen sponge," *Obstet. and Gynecol.* 56: 503–506 (1980).
Williams, W. L., "New antifertility agents active in the rabbit vaginal contraception method," *Contraception* 6(22): 659–672 (1980).

*Primary Examiner*—Michael A. Brown
*Attorney, Agent, or Firm*—Patrick D. Kelly

[57] ABSTRACT

This invention relates to the use of a water-soluble zinc salt, such as zinc acetate or zinc propionate, as an anti-viral agent in condom lubricants. Such lubricants can be coated onto condoms during manufacture and enclosed within condom packages, to provide an additional level of protection (beyond the level of protection already provided by the condom). The anti-viral zinc salt will help reduce the risk that a previously uninfected person will become infected by genital herpes viruses; it may also reduce the risk of transmission of HIV, hepatitis, and papilloma viruses, and other sexually transmitted pathogens.

5 Claims, 1 Drawing Sheet

CONDOM LUBRICANTS CONTAINING ZINC AS AN ANTI-VIRAL AGENT

This is a continuation-in-part of U.S. application Ser No. 737,169, filed on Jul. 29, 1991, which issued as U.S. Pat. No. 5,208,031 on May 4, 1993. That application was a continuation-in-part of application Ser. No. 528,495, filed on May 25, 1990, now abandoned, which was a continuation-in-part of application Ser. No. 362,058, filed on Jun. 6, 1989, also abandoned.

BACKGROUND OF THE INVENTION

This invention is in the fields of biochemistry, pharmacology, and anti-viral agents.

The background information and teachings contained in above-cited application Ser. No. 737,169 (now U.S. Pat. No. 5,208,031) is incorporated herein by reference. That application describes topical lubricants which are spread on the surfaces of the genitals before and during sexual intercourse, which contain a water-soluble zinc salt as an anti-viral agent. The lubricant must be non-irritating, physiologically acceptable, and free of adverse long-term effects when used in this manner.

The zinc salt must release zinc ions at an effective concentration that reduces the risk of sexual transmission of herpes simplex virus from an infected person to an uninfected person (as indicated by its ability, at similar concentrations, to inhibit the infectivity or replication of herpes viruses in in vitro cell culture tests or in in vivo animal tests). Preferred organic salts include zinc acetate and zinc propionate, which are highly soluble in water, and which have low pK values (which indicates high levels of ionic dissociation to release the ion, $Zn^{++}$). Other organic salts that are less preferred but which can be used if desired include zinc butyrate, formate, gluconate, glycerate, glycolate, and lactate. Another salt that may be suitable for use by some people comprises zinc sulfate; however, it causes irritation in some people, and is not preferred.

Prior to this invention, numerous researchers reported that zinc could inhibit herpes viruses in cell culture tests (e.g., Gordon et al 1975, Shlomai et al 1975, Gupta and Rapp 1976, Fridlender et al 1978, and U.S. Pat. No. 4,407,818 (Lionelle et al)) or in previously-infected people or animals (e.g., DeRoeth et al 1963, Jones 1979, Tennican et al 1979 and 1980, Fahim et al 1980a and 1980b, Wahba et al 1980, Brody et al 1981, Eby and Halcomb 1985, and U.S. Pat. Nos. 4,465,666 and 4,762,715 (Lukas et al)).

Most of that work was done before the advent of nucleoside analogs such as acyclovir and gancyclovir; interest in zinc as a topical anti-herpetic treatment dropped off sharply after nucleoside analogs offered a more effective oral treatment. Most of the above-cited reports involve zinc sulfate, which causes genital irritation in most users, and none of them disclose or suggest the use of zinc as a preventive agent for use in genital lubricants during intercourse, to reduce the risk of transmission to someone not previously infected. That type of preventive use was the subject of co-pending application Ser. No. 737,169, which is not prior art against this application.

The molecular mechanism by which zinc inactivates herpes viruses (and, apparently, the human immunodeficiency virus, abbreviated as HIV, the causative agent of AIDS) is believed to involve the formation of crosslinking bonds. Zinc, a positively charged ion, binds to unshared electron pairs on the residues of certain types of amino acids (including cysteine, histidine, glutamine, and asparagine) in proteins. This crosslinking reaction cause viruses to agglomerate, precipitate, and bind to each other and to various types of cells that cannot be infected. This reduces the ability of the crosslinked viruses to infect susceptible cells.

The foregoing is discussed in more detail in application Ser. No. 737,169 (now U.S. Pat. No. 5,208,031).

Addendum to U.S. Pat. No. 5,208,031: Physiology and Toxicology

The following paragraphs summarize (1) a major review article on zinc physiology and toxicology, which was published in early 1993, and (2) items of prior art that came to the Applicant's attention after application Ser. No. 737,169 was filed. The prior art was cited in application Ser. No. 737,169; since prior art statements are not published as part of a patent, they are summarized below, since they shed more light on the invention.

An extensive review article which discusses the molecular activities and biochemical effects of zinc was published in January 1993 (Vallee and Falchuk 1993). Among other things, this report concluded that zinc is "virtually nontoxic" inside the body. Toxicity problems can arise in unusual situations, such as inhalation of zinc fumes by metalworkers, genetic defects that render certain people unable to metabolize zinc properly, and problems related to zinc deficiency, but such problems are rare, and in healthy people, toxicity caused by excessive zinc is virtually nonexistent. Since zinc is an essential cofactor in hundreds of mammalian proteins, it is carefully regulated by the body; this is in contrast to other transition metals, such as copper and iron, which cause substantial toxicity if their concentrations exceed certain limits. If zinc in the blood exceeds preferred levels, at least two major factors reduce it to preferred levels: (1) zinc secretion in the urine and feces rises, and (2) it stimulates the expression of chelating proteins such as metallothionein, which efficiently sequester the zinc in inactive form. Zinc can also bind reversibly to numerous other proteins as well, which further helps maintain homeostatic equilibrium. These factors provide efficient mechanisms for controlling or eliminating excess zinc. As stated in another review article, "Toxicity of zinc is low . . . zinc is not mutagenic and has little, if any clastogenic properties . . . zinc is not teratogenic; it can, in fact, avert teratogenicity of other agents. Conversely, zinc deficiency may be harmful" (Leonard et al 1986). Other toxicological and physiological analyses include Vallee 1988, Mills 1989, and Bach 1981.

The great majority of zinc in the body is in cohesive tissue, primarily skeletal muscle and bone. Zinc in the blood constitutes less than 0.5% of total body zinc. About 80 to 90% of blood zinc is either inside cells or bound to cell surfaces. In the plasma, which contains about 1 ug/gram of zinc, the great majority of soluble zinc is bound to proteins such as albumin, alpha macroglobulin, and transferrin.

A few reports refer to zinc as a "heavy metal." This apparently is based on an arbitrary classification in which any metal with a molecular weight higher than iron (MW 56) is called a heavy metal. However, "heavy metal" is misleading, since it implies "toxic and dangerous" to many readers. The archetype heavy metals are mercury, cadmium, lead, uranium, and plutonium; clearly, zinc does not belong in the same category with those. Accordingly, zinc should be called a transition metal, or an essential mineral.

In addition to the Vallee and Falchuk review, which focuses mainly on zinc in blood and internal tissues, numerous reports state that zinc can help stabilize and protect cell membranes. The molecular mechanisms apparently include protecting sulfhydryl groups against oxidation, inhibiting the production of oxidative free radicals, and inhibiting the leakage of metabolites out of pores or other lesions created by certain bacteria and viruses (Chvapil 1973 and 1976; Mahadevan et al 1990; Bray and Bettger 1990; Pasternak et al 1992; Kaszuba and Hunt 1990). Zinc also increases the integrity of multicellular membranes in the body, such as blood vessel walls (Hennig et al 1992). Zinc also promotes the activity of numerous enzymes that help cells withstand stress, such as glucose transporters (Pasternak 1990), ecto-nucleotidases (Meftah et al 1991), and protein kinases (Zalewski 1991). An extensive review of the beneficial effects of zinc in promoting the growth of epidermal cells and the healing of skin deficits (such as cuts and wounds, decubitis ulcers (such as bedsores), rashes, and other lesions is provided in Agren 1990.

Zinc is widely used as a soothing/healing/protective agent in topical formulations that are applied to the skin, such as ointments, lotions, creams, and powders. For example, zinc is the active ingredient in calamine lotion, sunblocking creams, various anti-fungicidal or anti-bacterial ointments and powders, and ointments for treating diaper rash. Parents have been spreading zinc ointments directly onto the genitals of their babies, to cure diaper rash, for decades; this provides a valid indication of its absence of toxicity, and of its soothing and healing properties, when applied to the surface of the skin even in highly sensitive areas. Some topical forms sold over-the-counter contain more than 30% elemental zinc, by weight. Most topical forms contain zinc oxide, which gradually solubilizes and releases zinc ions when it contacts body fluids (Agren 1990).

In short-term tests, zinc has been shown to be harmless or beneficial inside the vagina (Chvapil et al 1978a and 1978b; also see Williams 1980 and Chvapil 1980). These reports describe research using guinea pigs, rabbits, and human volunteers to study whether zinc might be effective as a contraceptive. It was only about 80% effective on a single-event basis, so interest in contraceptive use died out; however, those reports indicated that (1) most of the zinc introduced into the vagina apparently became bound to vaginal fluids and exfoliated cells, and was washed out during the following days by the natural exudation of fluid from the vagina; (2) zinc content in vaginal tissue in treated animals was not significantly different than in control animals; and, (3) it did not cause any significant swelling, redness, tenderness, or histological changes to vaginal membranes. Indeed, when introduced into the vagina along with other contraceptive agents, zinc showed beneficial effects, by reducing or preventing the irritation or swelling caused by the other agents. This is consistent with the activity of zinc as a topical healing agent.

On the subject of vaginal tissue, it should be noted that the mucous membranes which coat the interior surfaces of the vaginal cavity are epithelial cells, rather than epidermal cells. Unlike epidermal cells, which lose their nuclei as they divide from basal cells below the epidermis, epithelial cells retain their nuclei as they approach and then reside on the outermost surface of a mucous membrane. However, those nuclei become attenuated and pyknotic, which means that the nuclei become inactive, compacted, and unable to carry out the normal chromosomal functions of replication and transcription.

Furthermore, epithelial cells remain on the surface for only a short period, and are constantly exfoliating (i.e., they detach and are shed by the membrane) and being replaced by new cells coming up from below. Reports such as Averette et al 1970 and Ferenczy and Guralnick 1979 state that inside the vagina, cells typically remain on the interior surfaces for only about 4 days before they detach and wash away. That period is even shorter in women being treated with hormones such as estrogen.

In healthy men, zinc is present in semen at concentrations of 100 to 500 ug/g, and in prostate fluid at concentrations up to 1000 ug/g (Eliasson and Lindholmer 1971; Fair et al 1976; Homonnai et al 1978; Marmar et al 1980). These concentrations are extraordinarily high compared to blood plasma, which contains only about 1 ug/ml zinc, and it indicates that dermal and epithelial membranes in the genital areas are adapted to withstand high concentrations of zinc. The roles and effects of these high concentrations are not fully understood; they apparently have some antimicrobial effects, and they also suppress the respiration (and therefore the metabolic activity and motility) of sperm cells (Eliasson 1971; Paz et al 1977). After ejaculation, sperm-associated zinc is diluted by other fluids, and it binds to various proteins inside the vagina. This reduces the concentration of sperm-associated zinc, allowing the activity and motility of the sperm to increase. The result, apparently, is that zinc provides a chemical method of keeping sperm cells in a quiet state, so they can conserve their energy until needed.

The high zinc concentrations in seminal fluid are relatively toxic to lymphocytes. This is not surprising, since zinc levels in blood are carefully regulated, and most lymphocytes never encounter the zinc concentrations that occur in semen. However, some lymphocytes do appear in ejaculates, and they apparently play an important role in transmission of HIV. The survival time of lymphocytes in ejaculates are likely to be longer in men suffering from AIDS-related reductions of the zinc levels in their semen (Weiner 1984 and Fabris et al 1988).

In this invention, the toxicity to lymphocytes of high levels of zinc in a topical lubricant apparently will be beneficial. HIV-infected lymphocytes appear to pose a greater threat of establishing an infection than free HIV particles; see Pearce-Pratt and Phillips 1993, Zagury et al 1985, Ho et al 1985, and Levy 1988. This increased risk is due to cell-cell binding reactions which allow infected lymphocytes to bind to and inject viruses into epithelial cells, which do not have CD4 receptors on their surfaces. By contrast, free HIV particles floating in a biological fluid can only infect cells that have CD4 receptors on their surfaces, and the viral particles must contact and bind to those particular receptors. Therefore, if non-physiologic concentrations of zinc in a topical lubricant used during intercourse can kill lymphocytes, this apparently would eliminate or reduce the ability of HIV-infected lymphocytes to establish cell-mediated infections in epithelial cells.

One object of this invention is to disclose an article of manufacture comprising a condom which is enclosed within a watertight package with a hydrophilic lubricant containing a non-irritating water-soluble zinc salt at a concentration that can reduce the risk that a previously uninfected person will become infected by a sexually transmitted virus such as herpes or possibly HIV.

SUMMARY OF THE INVENTION

This invention relates to the use of a water-soluble zinc salt, such as zinc acetate or zinc propionate, as an anti-viral agent in condom lubricants. Such lubricants can be coated onto condoms during manufacture and enclosed within condom packages, to provide an additional level of protection (beyond the level of protection already provided by the condom). The anti-viral zinc salt will help reduce the risk that a previously uninfected person will become infected by genital herpes viruses; it may also reduce the risk of transmission of HIV, hepatitis, and papilloma viruses, and other sexually transmitted pathogens.

DETAILED DESCRIPTION OF THE INVENTION

Figure 1:
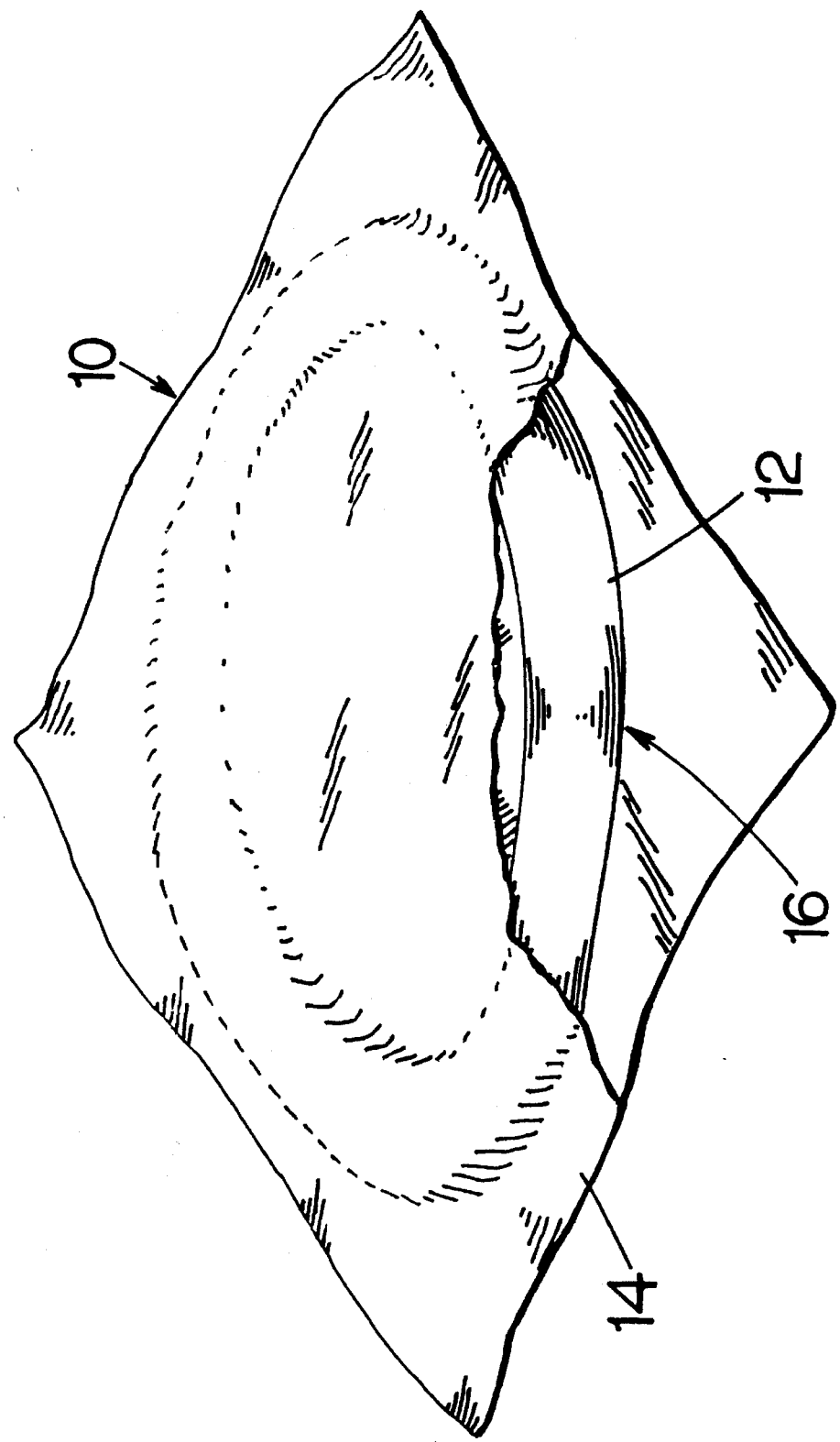
FIG. 1 is a perspective view showing an article of manufacture 10 as claimed, comprising a condom 12 contained within a sealed package 14 (shown in a partial cutaway view) which also encloses a lubricating fluid 16 that contains a suitable zinc salt.

This invention relates to the use of zinc salts as anti-viral agents in condom lubricants. Such lubricants can be coated onto condoms during manufacture and enclosed within condom packages, such as the conventional watertight plastic or metallic foil packages that contain one condom per package. When used as a condom lubricant in this manner, the zinc-containing condom lubricant will provide an added level of protection, beyond the protection already provided by the condom, that will further reduce the risk that a previously uninfected person will become infected by a sexually transmitted virus such as a herpes virus during or after intercourse with an infected person.

The effectiveness of zinc salts in inhibiting herpes viruses has been established by previously published reports, which describe both in vitro and in vivo tests. Such reports include DeRoeth et al 1963, Gordon et al 1975, Shlomai et al 1975, Gupta and Rapp 1976, Fridlender et al 1978, Jones 1979, Tennican et al 1979 and 1980, Fahim et al 1980a and 1980b, Wahba et al 1980, Brody et al 1981, and Eby and Halcomb 1985, as well as U.S. Pat. Nos. 4,465,666 and 4,762,715 (Lukas et al) and 4,407,818 (Lionelle et al). None of those reports or patents disclose or suggest the use of zinc salts as preventive agents for use in sexual lubricants, to reduce the risk of infection. Most reports involve the use of zinc sulfate, which causes genital irritation in most users, and all in vivo tests involved humans suffering from active outbreaks, or lab animals that were infected by viruses prior to administration of the zinc compounds.

In addition to reducing the risk of infection by herpes viruses, zinc salts may also be able to reduce the risk of infection by the human immunodeficiency virus (HIV, the causative agent of AIDS), and by other sexually transmitted viruses as well, such as hepatitis and papilloma viruses. Examples 2 through 4, below, provide data indicating that in cell culture tests, zinc salts inactivated the human immunodeficiency virus (HIV), the causative agent of AIDS. In addition, topically administered zinc has long been known to have general antibacterial and antifungal effects, and to promote growth of epidermal cells and closure of skin wounds rashes, or ulcers; accordingly, the zinc-containing lubricants of this invention may also help reduce the risk of sexual transmission of various non-viral pathogens, such as gonorrhea, syphilis, chlamydia, and mycoplasma. If such additional benefits occur, they will provide additional utility to the invention; however, this invention does not depend upon the ability of zinc to inhibit HIV or any other pathogen, since inhibition of any type of sexually transmitted pathogen, such as herpes viruses, can provide sufficient utility to support patentability.

As used herein, "condom" refers to a barrier device which is used on a one-time, disposable basis to provide a watertight physical barrier between male and female genitalia during sexual intercourse, and which are removed after each act of intercourse. This term includes conventional condoms used to cover a penis prior to intercourse; it also includes so-called "female condoms" which are inserted into the vaginal cavity on a one-time, disposable basis prior to intercourse. The term condom does not include diaphragms, cervical caps, or other barrier devices which cover only a portion of the epithelial membranes inside the vaginal cavity. Preferably, such condoms should be made of latex, which provides a higher degree of protection against sexually transmitted viruses than so-called "lambskin" or "natural membrane" condoms.

As used herein, "condom lubricant" refers to a physiologically acceptable, fluidized substance which is spread across one or more surfaces of a condom and which is contained within a watertight package that contains a condom. It does not include compounds that are spread onto the surface of a condom after a condom has been removed from the package used to ship and sell the condom.

When the condom lubricants of this invention are used during intercourse, the zinc ions released by the zinc salt dissolved in the lubricant will reduce the risk that an uninfected person will become infected by genital herpes if the sexual partner emits herpes simplex virus. This invention relates to the discovery that some zinc salts that are soluble in aqueous solutions do not irritate the skin or mucosal membranes of the penis or vagina, even when a lubricant mixture containing such a salt is rubbed in over a sustained period of time, as occurs during intercourse.

Since the anti-vital activity of the zinc ions disclosed herein depends on the ionization of water-soluble salts, the condom lubricants of the subject invention are limited to (1) water-soluble lubricants, in which all components of the fluid have a substantial degree of solubility in water, and (2) emulsions, in which an aqueous phase is mixed with an immiscible (hydrophobic) phase (see, e.g., Becher 1965). In an emulsion, microscopic droplets of one phase are usually suspended (often with the help of an emulsifying agent) in a matrix comprising the other phase. Emulsions are usually more expensive than simple aqueous mixtures, and they can leave undesired residues or cause adverse long-term effects due to their hydrophobic components or emulsifying agents. Accordingly, they are not preferred for use as described herein, but they can be used if desired.

In addition to a zinc salt, a condom lubricant preferably should contain at least one "lubricating agent" which is incorporated into the mixture for the purpose of reducing friction during intercourse. Although any liquid (including water) can sometimes function as a "lubricant" in the broadest sense of the word, four characteristics distinguish a "lubricating agent," as that term is used herein, from water and other liquids that do not have the characteristics necessary for effective lubrication in the context of sexual intercourse: (1) a lubricating agent feels slippery and is substantially more viscous than water when rubbed between two skin surfaces; (2) a lubricating agent should have an affinity for human skin, and when applied to skin, it should spread smoothly and evenly across the contacted area; (3) a lubricating agent should remain in contact with the skin, clinging to it in a more substantial manner than water, which is easily wiped away; and, (4) a lubricating agent should have a low level of volatility, and should not evaporate quickly. The foregoing characteristics can easily be recognized and understood on a practical level by rubbing a lubricating agent such as glycerin or mineral oil between the fingers. The nature and the durability of the lubrication provided by such a compound, and the differences between such agents and other liquids such as water, are readily apparent. In addition, in order to be physiologically acceptable, a selected lubricating agent should not cause any significant adverse effects (such as irritation, tenderness, swelling, redness, or skin discoloration), and must not pose a significant risk as a carcinogen or teratogen. Further, in contrast to non-physiological lubricants such as motor oil, physiologically acceptable lubricating agents should be either gradually broken down into innocuous substances in the body, if they are absorbed through the skin or mucous membranes, or they should be of a nature that allows them to be secreted by the vagina and washed cleanly from the skin, so that they will not foul and clog the pores in membranes or dermal layers.

Several lubricating agents which are used in commercially available sexual lubricants satisfy these criteria, including glycerin (also called glycerine, glycerol, 1,2,3-propanetriol, and trihydroxypropane) and certain types of polyethylene glycol (PEG), such as PEG 200 or PEG 400 (the numbers indicate different molecular weight averages). Various other polymers (such as polypropylene glycol, polyisobutene, and polyoxyethylene) and behenic acid and behenyl alcohol are also used as lubricants in cosmetics and other formulations that contact the skin. In addition, some sugar-alcohols such as sorbitol and some silicon compounds such as polydimethylsiloxane are also used as skin-contacting lubricating agents.

Because glycerin, propylene glycol, polyethylene glycol, and polypropylene glycol have long been used in sexual lubricants and other skin-contacting formulations with no adverse effects, they are preferred for use as lubricating agents in the anti-viral sexual lubricants of this invention. The suitability of any other candidate lubricating agent as a condom lubricant as described herein can be determined through routine experimentation in humans to ensure that it will not cause irritation or other adverse effects, and in in vivo tests as described below to ensure that a formulation containing the candidate lubricating agent is anti-virally effective.

Other components, including preservatives (such as chlorhexidine gluconate), anti-crystallization agents (such as glucono-delta-lactate), fragrances, coloring agents, alkaline or acidic agents to maintain the proper pH, and soothing or anti-swelling agents (such as lanolin, aloe vera extract, or hydrocortisone) can be added to the condom lubricants described herein, provided that (1) any such additive should not seriously impede the anti-viral activity of the selected zinc salt due to reactions such as chelation or the formation of covalently-bonded zinc-containing molecular complexes, and (2) the additive should not irritate or have other adverse effects on the genitals.

Zinc Salts

When the lubricants of this invention are used during intercourse, the $Zn^{++}$ ions released by the zinc salt will reduce the risk that an uninfected person will become infected by viruses such as herpes viruses if the sexual partner is infected. As mentioned above and as discussed in more detail in application Ser. No. 737,169 (now U.S. Pat. No. 5,208,031), the anti-viral activity of zinc is presumed to be due to its ability to form random crosslinking bonds with unshared electron pairs on certain types of amino acid residues in proteins. This crosslinking activity can cause viral particles to agglomerate with each other and bind to the surfaces of cells which they cannot infect or which are dying and which will soon be exfoliated from the surface of the skin or a mucous membrane.

Three factors are important in determining the concentration of zinc ions that will be present in an aqueous carrier substance if a certain salt is dissolved in the carrier substance. Those factors are:

(1) The solubility of the zinc salt in water. This value is often expressed in terms of grams of salt per 100 cubic centimeters (0.1 liter) of saturated solution. That Figure can be converted into a grams/liter basis by multiplying it by 10.

(2) The molecular weight of the salt, which allows a weight concentration to be converted into a molar concentration. For example, the molecular weight of zinc acetate is 183.4, so 183.4 grams of zinc acetate is equal to one mole ($=6.02 \times 10^{23}$ molecules). Molar concentrations are usually expressed in molar (M) units, which refer to moles of a compound per liter of solution, or in millimolar (mM) concentrations, which refer to thousandths of a mole per liter.

(3) The rate at which the salt dissociates into cations and anions. This is usually expressed on a base 10 logarithmic scale using pK values, which are often called equilibrium constants, stability constants, or dissociation constants. If a pK is low, the rate of ionic dissociation for that particular salt is high.

Solubility and pK values for several zinc salts are provided in Table 1. These values were obtained from published reports (Sillen and Martell 1964 and 1971, Lide 1990, Linke 1965, and Cannan and Kibrick 1938). From a review of several articles cited by Sillen and Martell, it appears that (1) reported pK values of less than 2 refer to the release of a single carboxy anion from a zinc salt, and (2) reported pK values of more than 2 (e.g., Griesser et al 1968) apparently refer to the release of divalent zinc ions by dissociation of two carboxy anions. There are several methods for measuring ion concentrations, and variations in values between different published papers reflect differences in the method of measurement.

Since zinc gluconate has already been reported to be effective in combatting established herpes infections, it can be regarded as a benchmark of effectiveness. Other zinc salts that are comparably soluble (or preferably more soluble) and which have comparable (or preferably lower) pK values, when compared to zinc gluconate, can be presumed to be effective in inhibiting herpes virus. The anti-viral effectiveness of any such zinc salt in aqueous solution, or in a complete lubricant formulation, can be tested using in vitro tissue culture tests or in vivo animal tests as described in the above-cited parent application.

All of the organic zinc salts listed in Table 1 are good candidates for use in anti-viral lubricants as described herein. Two preferred salts that have high solubility in water, and high ionic dissociation (low pK values), are zinc acetate and zinc propionate.

Among other things, this invention relates to the discovery that certain zinc salts that are soluble in water do not irritate the skin or mucosal membranes of the penis or vagina, even when a lubricant containing such a salt is rubbed into the skin or membrane over a sustained period of time, as occurs during intercourse. Zinc acetate and zinc propionate were both tested for irritation; although each of them caused vaginal irritation when dissolved in water alone, they were found to be non-irritating when mixed with K-Y Lubricating Jelly at concentrations up to about 5% weight/volume and used as a lubricant during intercourse. Zinc butyrate also has a high rate of ionic dissociation; since it is less soluble than zinc acetate or propionate, it was not tested for irritation.

Zinc gluconate was also tested and did not cause any irritation during intercourse. However, it does not have a high degree of solubility in water, and when extensively ground in a mortar and pestle, it generated fine particles which displayed a very slight roughness when rubbed hard between the forefinger and thumb. Although no abrasion or irritation was noticeable by either person during intercourse, it is not recommended for use in a lubricant, due to the risk of creating microabrasions that might help viral particles penetrate skin or mucous membranes.

Other organic salts that appear to be less preferred, since they are less soluble in aqueous solution and/or because they have relatively high pK values, include zinc salicylate, zinc citrate, zinc oleate, zinc benzoate, zinc laurate, and zinc tartrate. Several other organic salts of zinc were obtained and evaluated, including zinc stearate, zinc salicylate, and zinc valerate. None of those salts caused any irritation during forearm or male genital tests; however, each had other drawbacks. Zinc valerate, although soluble in water, has an unappealing dirty-looking color and an unpleasant odor. Zinc stearate and zinc salicylate have very low solubility in water, and also have unpleasant odors. Accordingly, even though they caused no irritation in forearm or male genital tests, they were not tested vaginally or during intercourse.

Lubricants Having A Range of Zinc Concentrations

Rather than trying to determine a single concentration of a zinc salt that would be optimal for everyone, the effectiveness of this invention can be enhanced by selling lubricants having a range of different zinc concentrations for different people. By way of analogy, since some people are easily sunburned while others are highly tolerant of direct sunlight, suntan oils and creams are sold with a range of "sun protection factors" and any purchaser is free to choose his or her preferred formulation, based not only on skin type, but also on his or her anticipated exposure. As another example, contraceptive gels containing 1% to 4% nonoxynol, and condoms lubricated with fluids containing 5 to 15% nonoxynol, are both sold over-the-counter, and purchasers are free to choose the concentration they prefer.

In a comparable manner, sexual lubricants having a range of concentrations of anti-viral zinc salts can be made available, and people having varying sensitivities, sexual habits, and levels of concern over sexually transmitted viruses can choose the concentrations they prefer. While people who are at relatively low risk or who have sensitive skin or a high susceptibility to psychosomatic suggestions of irritation, might prefer to use a formulation having a lower concentration, such as about 0.5% to 3%, expressed as weight per volume (w/v, calculated as grams of zinc salt per milliliter of fluid, multiplied by 100 to convert the ratio to a percentage). People who are highly sexually active and non-monogamous, or who live in cities with high rates of sexually transmitted diseases, might choose to use a lubricant containing 30% or more of a zinc salt. This figure might seem high, but it should be noted that:

(1) it indicates the weight of the salt rather than zinc only; a compound containing 30% zinc acetate would contain about 10.7% zinc;

(2) preparations used for other surface applications are sold over-the-counter which contain more than 30% elemental zinc; and, (2) the quantity of lubricant fluid in a condom package is small, and any such lubricant is diluted when intercourse begins. For example, while spermicidal gels usually contain about 5% nonoxynol (or less) as a spermicide, condom lubricants contain up to 15% nonoxynol. In the same manner, a zinc-containing condom lubricant preferably should have a somewhat higher concentration of zinc than an aqueous gel.

Accordingly, this invention anticipates condom lubricants containing zinc salts in the range of about 0.5% to about 30% w/v.

As used herein, references to "non-irritating" refer to formulations that cause no irritation, or acceptably low levels of irritation, in at least some people. Such formulations can be used by such people regardless of whether they might cause irritation in other people who are more susceptible. In addition, the anti-viral lubricants of this invention can be used even though they may cause some irritation in the user; many people would regard a low level of mild irritation as a reasonable and necessary price for an added level of safety, comparable to the loss of sensitivity that accompanies condom use.

Anyone buying such a lubricant should be clearly warned that the lubricant does not offer completely reliable, 100% protection against herpes infection. Nevertheless, the anti-viral sexual lubricants of this invention can reduce the risk of becoming infected. Accordingly, in the absence of any effective vaccines or cures for herpes or AIDS, most rational people who are sexually active and non-monogamous would prefer to take the precaution of using a non-irritating lubricant which offers a significant level of added protection.

EXAMPLES

EXAMPLE 1

Genital Irritation Tests

Several examples discussing skin and genital irritation tests are described in above-cited U.S. Pat. No. 5,208,031. Those examples are incorporated by reference. Briefly, zinc acetate, propionate, and gluconate caused no irritation when used as lubricants during heterosexual intercourse between human volunteers, when mixed with K-Y Lubricating Jelly (Johnson & Johnson, New Brunswick, N.J.) at concentrations up to about 5% w/v.

EXAMPLE 2

High-Titer HIV Infectivity Tests

HIV tests were carried out at Biotech Research Laboratories (Rockville, Md.). The HIV-1 vital isolate and H-9 cell line were originally supplied by R. Gallo of the NCI.

In a first set of tests, 20 mg of zinc acetate powder (ZnAc, MW 183.4) was mixed in 1 ml RPMI cell culture medium (Whittaker Corp.). This 2% (w/v) salt mixture contained 7 mg/ml elemental Zn. Although ZnAc is highly soluble in water, it generated a precipitate in the culture medium, which contains protein. Therefore, a small quantity of HCl was added until the mixture became clear; the pH was about 5.5. The Zn concentration was reduced by half (and the pH was raised somewhat) when an equal volume (1 ml) of cell-free HIV-1 stock was added. The zinc/virus mixture was stirred and incubated for 2 hours at 37° C.

Following this first incubation step, the zinc/virus mixtures were diluted at 1:10, 1:30, and 1:100 ratios using culture medium, and aliquots were added to equal volumes of culture media containing H-9 lymphocytes that had been pretreated overnight with 2 ug/ml Polybreen. The lymphocyte mixtures were incubated for three hours at 37° C.; zinc concentrations during this step were 180, 60, and 18 ug/ml for the 1:10, 1:30, and 1:100 dilutions.

The cell aliquots were then washed twice, using culture medium, to remove free p24 proteins that are present in the initial viral stock. Such proteins will skew ELISA readings if not removed by washing. Cells were then resuspended in fresh medium containing 10% fetal calf serum (FCS) and cultured for 20 days. During this period, each tube was periodically sampled by hand-mixing the tube, withdrawing 100 ul of liquid from the top, and testing the sample for p24 antigens using ELISA assays.

The 1:10 dilutions, which contained 180 ug/ml Zn during the 3-hour incubation prior to washing, caused substantial mortality to the lymphocytes, and resulting ELISA data were discarded.

Based on visual observations, 1:30 dilutions (60 ug/ml Zn) retarded cell growth during the first few days; however, any such effect disappeared within a few days and the cells grew well during the rest of the assay period.

A positive control was used at each dilution. Viral aliquots not treated with zinc were identically diluted, mixed with lymphocytes, cultured, and tested. Negative controls were also run, in which H-9 cells were plated and grown in the absence of any virus or zinc; these provided background levels that vary slightly from day to day, depending on factors such as spectrophotometer calibrations and rinsing conditions.

Optical density (OD) data from the 1:30 dilution test are shown in FIG. 1. These quantities are averages based on triplicate samples. The p24 concentrations were indistinguishable from background levels, which indicates that the zinc treatment completely abolished viral infectivity.

Data from the 1:100 dilution test are shown in FIG. 2. One of the tubes became infected by mold after the 10th day, so subsequent values are based on averages from two samples. These results indicated that the zinc suppressed and retarded HIV infectivity; however, apparently, some small fraction of the viruses apparently remained infective.

EXAMPLE 3

Diluted HIV Infectivity Tests

The tests described above, in Example 2, used an undiluted high-titer viral stock, which contained at least ten million infectious vital particles per ml. That concentration can be achieved in a laboratory only by special culturing, purification, and concentration techniques, and it is vastly higher than would actually occur in the ejaculate of an HIV-infected person (especially someone who is not in the end stages of the disease, and who might pose a significant risk of transmitting the virus to an uninfected sexual partner).

In subsequent tests, ZnAc was tested against diluted viral stocks and completely abolished the infectivity of the infected viruses. These tests used serial dilutions of the viral stocks, at ranges up to 1:10,000. To create the 1:10 dilution, 500 ul of viral stock was mixed with 4.5 ml of RPMI mediums. Subsequent dilutions added 9 ml of RPMI medium to 1 ml from the preceding dilution.

A 2 ml aliquot from each dilution was mixed with an equal volume of 3% ZnAc dissolved in sterile distilled water; after mixing, the zinc concentration was 5.3 mg/ml Zn. These mixtures were incubated for 2 hours, then diluted with culture medium at 1:30, 1:100, and 1:1000 to reduce the toxicity of the zinc to lymphocytes. Four ml of lymphocytes were mixed with 4 ml of each zinc/virus mixture. The zinc/virus/cell mixtures were incubated at 37° C. for 3 hours; zinc concentrations were 88, 27, and 2.7 ug/ml in the 30, 100, and 1000 dilutions. During subsequent culturing, significant cell mortality was observed in the 88 ug/ml treatment batch, but no cell mortality was observed at the lower levels.

Following the 3 hour incubation, the cells were washed twice in RPMI medium and resuspended in fresh medium containing 10% FCS. Each solution was inoculated (2 ml; estimated minimum $2 \times 10^5$ cells per well) into each of three wells in a 12-well plate and cultured for 27 days, with periodic sampling and measuring of p24 antigens.

ELISA data for the 10×, 100×, and 1000×high-titer viral stock dilutions, treated with the 1000×dilution of the zinc/virus mixture (2.7 ug/ml Zn final concentration) are shown in FIG. 3. As shown, the zinc treatment completely blocked infectivity. Data for the diluted viral stocks treated with 1:100 zinc/virus dilutions (27 ug/ml Zn) were virtually identical; viral infectivity was completely blocked in those tests as well.

Negative controls were identically diluted cells that did not contain zinc or HIV. Positive controls which used 1:1000 dilutions of viral stock mixed with zinc-free RPMI were consistently highly infectious, even though their concentrations were 100×lower than the 1:10 mixtures in which infectivity was eliminated by zinc treatment. Other positive controls were tested at up to 100,000×dilutions; these were highly infective in two out of the three plates tested.

While carrying out the viral dilution tests, tests were also performed using 2 ml of 3% ZnAc solution in distilled water mixed with 2 ml aliquots of undiluted viral stock. The zinc/virus mixtures were incubated for 2 hours, diluted with RPMI at 1:100 and 1:1000 ratios, and mixed with lymphocytes for three hours; zinc concentrations were 27 and 2.7 ug/ml. The cells were washed twice, inoculated into 12 well plates as described above, and cultured for 27 days. ELISA results are shown in FIG. 4. As shown, the 1:100 dilution (27 ug/ml Zn) completely prevented infectivity, while the 1:1000 dilution (2.7 ug/ml) delayed the onset of infection.

EXAMPLE 4

HIV Precipitation Tests

Precipitation tests were also performed, using 2% ZnAc which was mixed with an equal volume of undiluted viral stock, incubated for 24 hours, and centrifuged at 1500 rpm in a tabletop centrifuge for 5 minutes. The supernatant was sampled (100 ul) and serially diluted by medium, at 1:10 followed by 2×dilutions (1:20, 1:40, 1:80, etc) to a maximum dilution of 1:10240. Each dilution was analyzed spectrophotometrically to determine the concentration of viruses suspended in solution. After sampling, each tube was hand-mixed and incubated for 24 hours. The solution near the top of the tube was sampled again, serially diluted, and tested using the ELISA assay. The tube was hand-mixed again, incubated for three more days, and sampled again to obtain Day 5 values.

The values for zinc-treated viruses averaged about 40% less than values for identically diluted solutions that did not receive zinc treatment. This indicates that the zinc caused substantial precipitation of the virus and lowered the concentration of free HIV particles in solution.

Thus, there has been shown and described a new and useful method of reducing the risk of infection by sexually transmitted viruses, in people who were not previously infected. Although this invention has been exemplified for purposes of description and illustration by reference to certain specific embodiments, it will be apparent to those skilled in the art that various modifications and alterations of the illustrated examples are possible. Any such changes which derive directly from the teachings herein, and which do not depart from the spirit and scope of the invention, are deemed to be covered by this invention.

REFERENCES

Agren, M. S., "Studies on zinc in wound healing," *Acta Dermato-Venereology*, Supplement 154: 1–36 (1990)

Averette, H. E., et al, "Autoradiographic analysis of cell proliferation kinetics in human genital tissue," *Amer. J. Obstet . Gynec.* 108: 8–17 (1970)

Bach, J. F., "The multi-faceted zinc dependency of the immune system," *Immunology Today:* 225–227 (Nov. 1981)

Becher, P., *Emulsions: Theory and Practice,* 2nd ed., Amer. Chem. Soc. Monograph #162 (Reinhold Publ., New York, 1965)

Brawner, T. A., et al, "A Combined Chemical-Physical Treatment for Herpes Simplex Lesions in Guinea Pigs," *Arch. Dermatol. Res.* 265: 71–77 (1979)

Bray, T. M. and Bettger, W. J., "The physiological role of zinc as an antioxidant," *Free Radic. Biol. Med.* 8: 281–91 (1990)

Brody, I., "Topical treatment of recurrent herpes simplex . . . zinc sulphate solution," *Brit. J. Dermatol.* 104: 191–194 (1981)

Cannan, R. K., and Kibrick, A., "Complex Formation between Carboxylic Acids and Divalent Metal Cations," *J. Amer. Chem. Soc.* 60: 2314 (1938)

Chvapil, M., "New aspects in the biological role of zinc: a stabilizer of macromolecules and biological membranes," *Life Sciences* 13: 1041–1049 (1973)

Chvapil, M., "Effects of zinc on cells and biomembranes," *Med. Clin. North Amer.* 60: 799–812 (1976)

Chvapil, M., et al, "Reaction of vaginal tissue of rabbit and of cheek pouch of hamster to inserted collagen sponges treated with either zinc or copper," *Am. J. Obstet. Gynecol.* 130: 63–70 (1978)

Chvapil, M., et al, "Preliminary testing of the contraceptive collagen sponge,"*Obstet. and Gynecol.* 56: 503–506. (1980)

DeRoeth, A., "Treatment of herpetic keratitis,"*Am., J. Ophthalmol.* 56: 729–731 (1963)

Eby, G. A., and W. W. Halcomb, "Use of topical zinc to prevent recurrent herpes simplex infection: review of literature and suggested protocols," *Medical Hypotheses* 17: 157–165 (1985)

Eliasson, R. and Lindholmer, C., "Zinc in human seminal plasma," *Andrology* 3: 147 (1971)

Eliasson, R., "Effect of zinc on human sperm respiration," *Life Science* 10: 1317 (1971)

Fabris, N., et al, "AIDS zinc deficiency, and thymic, hormone failure," *JAMA* 259: 839–849 (1988)

Fahim, M., et al, "New Treatment for Herpes Simplex Virus Type 2: Male Patients," *J. Medicine* 9(3): 245–264 (1978)

Fahim, M., et al, "New Treatment for Herpes Simplex Virus Type 2: Female Patients," *J. Medicine* 11(2&3): 143–167 (1980)

Fahim, M. S. and Brawner, T. A., "Treatment of Genital Herpes Simplex Virus in Male Patients,"*Arch. Andrology* 4: 79–85 (1980)

Fair, W. R., et al, "Prostatic antibacterial factor, identity and significance," *Urology* 7: 169–177 (1976)

Ferenczy, A. and Guralnick, M. S., "Morphology of the human vagina," pp. 3–12 in *Biology of the Fluids of the Female Genital Tract*, ed. by F. K. Beller and G. F. B. Schumacher (Elsevier, N.Y. 1979)

Fridlender, B., et al, "Selective inhibition of herpes simplex virus type 1 DNA polymerase by zinc ions," *Virology* 84: 551–554 (1978)

Gordon, Y. J., et al, "Irreversible inhibition of herpes simplex virus replication in BSC-1 cells by zinc ions," *Antimicrob. Agents Chemother.* 8: 377–380 (1975)

Griessar, R., et al, *Inorg. Nuclear Chem. Letters* 4: 443 (1968)

Gupta, P. and Rapp, F., "Effect of zinc ions on synthesis of herpes simplex virus type 2-induced polypeptides," *Proc. Soc. Exp. Biol. and Med.* 152: 455–458 (1976)

Hennig, B., et al, "Zinc deficiency alters barrier function of cultured porcine endothelial cells," *J. Nutr.* 122: 1242–7 (1992)

Ho, D. D., et al, "Infrequency of isolation of HTLV-III virus from saliva in AIDS," *New Engl J. Med.* 313: 606 (1985)

Homonnai, Z. T., et al, "Prolactin and zinc in the human ejaculate," *Andrologia* 10: 66 (1978)

Jones, R., "Genital Herpes and Zinc," *Med. J. Australia,* Apr. 7, 1979, p. 286

Kaszuba, M. and Hunt, G .R., "Protection against membrane damage: a $^1$H-NMR investigation of the effect of $Zn^{++}$ and $Ca^{++}$ on the permeability of phospholipid vesicles," *J. Inorg. Biochem.* 40: 217–25 (1990)

Kono, R., and Nakajima, A., eds., *Herpes Viruses and Virus Chemotherapy: Pharmacolegical and Clinical Approaches*(Excerpta Medica, N.Y., 1985)

Leonard, A., et al, "Mutagenicity, carcinogenicity and teratogenicity of zinc," *Mutation Research* 168: 343–353 (1986)

Levy, J. A., "The transmission of AIDS: The case of the infected cell," *JAMA* 259: 3037–3038 (1988)

Lide, D. R., ed., *CRC Handbook of Chemistry and Physics,* 71st Edition (Boca Raton, Fla., 1990)

Linke, W. F., ed., *Solubility of Inorganic and Metal Organic Compounds,* 4th Edition Mahadevan, D., et al, "Protection against membrane-mediated cytotoxicity by calcium and zinc," *Am. J. Pathol.* 136: 513–20 (1990)

Marmar, J. L., "Values for zinc in whole semen, fractions of split ejaculate, and expressed prostatic fluid," *Urology* 16: 478–480 (1980)

Meftah, S., et al, "Ecto 5' nucleotidase as a sensitive indicator of human zinc deficiency," *J. Lab Clin. Med* 118: 309–316 (1991)

Mills, C. F., ed., *Zinc in Human Biology* (Springer-Verlag, N.Y., 1989)

Pasternak, C. A., "Transmembrane communication and disease," *Indian J. Biochem. Biophys.* 27: 363–4 (1990)

Pasternak, C. A., et al, "Membrane damage: Common mechanisms of induction and prevention," *FEMS Microbiol. Immunol.* 5: 83–92 (1992)

Pearce-Pratt, R. and Phillips, D. M., "Studies of adhesion of lymphocytic cells: Implications for sexual transmission of HIV," *Biol. of Reproduction* 48: 431–445 (1993)

St. Onge, D. and Gicquaud, C., "Research on the mechanism of interaction between actin and membrane lipids," *Biochem. Biophys. Res. Commun.* 167: 40–7 (1990)

Shlomai, J., et al, "Effect of zinc ions on the synthesis of herpes simplex virus DNA in infected BSC-1 cells," *Virology* 66: 330–335 (1975)

Sillen, L. G., and Martell, A. E., *Stability Constants of Metal Ion Complexes,* Special Publication No. 17 (The Chemical Society, London, 1964)

Sillen, L. G., and Martell, A. E., *Stability Constants of Metal Ion Complexes,* Special Publication No. 25 (The Chemical Society, London, 1971)

Tennican, P. O., et al, "The Diverse Effects of Topical and Systemic Administration of Zinc on the Virulence of Herpes Simplex Genitalis," *Life Sciences* 24: 1877–1884 (1979)

Tennican, P., et al, "Topical Zinc in the Treatment of Mice Infected Intravaginally with Herpes Genitalis Virus," *Proc. Soc. Exp. Biol. Med.* 164: 593–597 (1980)

Vallee, B. I., "Zinc: biochemistry, physiology, toxicology and clinical pathology," *Biofactors* 1(1): 31–36 (1988)

Vallee, B. I. and Falchuk, K. H., "The biochemical basis of zinc physiology," *Physiological Reviews* 73: 79–118 (1993)

Wahba, A., "Topical Application of Zinc Solutions: A New Treatment for Herpes Simplex Infections of the Skin?" *Acta Derm. Venerol. (Stockholm)* 60: 175–177 (1980)

Weiner, R. G., "AIDS and zinc deficiency," *JAMA* 252: 1409–1410 (1984)

Williams, W. L., "New antifertility agents active in the rabbit vaginal contraception method," *Contraception* 22: 659–672 (1980)

Zagury, D., et al, "Evidence for HTLV-III in T cells from semen of AIDS patients," *Cancer Res.* 45 (*suppl.*): 4595–4597 (1985)

Zalewski, P. D., "Regulation of protein kinase C by zinc-dependent interaction with actin," *Biochem. Int.* 24: 1103–10 (1991)

I claim:

1. An article of manufacture comprising a condom, a fluidized lubricant, and a watertight package containing the condom and lubricant, wherein the lubricant contains a zinc salt that releases zinc ions when dissolved in water, at an effective concentration which reduces the risk of sexual transmission of at least one sexually transmitted virus from an infected person to an uninfected person, and wherein the lubricant is physiologically acceptable and does not irritate genital surfaces or mucous membranes.

2. The article of manufacture of claim 1 wherein the zinc salt is selected from the group consisting of zinc acetate, zinc propionate, zinc butyrate, zinc formate, zinc gluconate, zinc glycerate, zinc glycolate, zinc lactate.

3. The article of manufacture of claim 1 wherein the zinc salt comprises zinc sulfate.

4. The article of manufacture of claim 1 wherein the zinc salt is present in the lubricating fluid at a concentration in the range of about 0.5 to about 30 percent, expressed as weight per volume.

5. An article of manufacture comprising a condom, a lubricant compound, and a watertight package containing the condom and lubricant, wherein the lubricant compound contains a zinc salt that releases zinc ions when dissolved in water, at an effective concentration which reduces the risk of sexual transmission of at least one sexually transmitted virus from an infected person to an uninfected person, and wherein the lubricant compound is physiologically acceptable and does not irritate genital surfaces or mucous membranes.

* * * * *

UNITED STATES PATENT AND TRADEMARK OFFICE
CERTIFICATE OF CORRECTION

PATENT NO. : 5,482,053  
DATED : January 9, 1996  
INVENTOR(S) : Patrick D. Kelly Page 1 of 6

It is certified that error appears in the above-indentified patent and that said Letters Patent is hereby corrected as shown below:

In Col. 5, line 5, "FIG. 1" should be --FIG. 5--. Also, Figure 1 should be renamed as Figure 5. Brief descriptions of Figures 1-4, which were omitted, appear on the next page, followed by Figures 1-4 on additional pages.

In Col. 6, line 27, delete "anti-vital" and insert --anti-viral--

UNITED STATES PATENT AND TRADEMARK OFFICE
CERTIFICATE OF CORRECTION

PATENT NO. : 5,482,053
DATED : January 9, 1996
INVENTOR(S) : Patrick D. Kelly

It is certified that error appears in the above-indentified patent and that said Letters Patent is hereby corrected as shown below:

Under "Brief Description of the Drawings" (col. 5), insert:

FIGURE 1 is a graph showing that HIV infectivity was eliminated when concentrated HIV stocks were incubated with 1% zinc acetate for 2 hours before the zinc-HIV mixture was diluted (1:30) and mixed with lymphocytes, as described in Example 2.

FIGURE 2 shows that HIV infectivity was reduced and delayed when concentrated viral stocks were incubated with 1% zinc acetate for 2 hours before the zinc-virus mixture was diluted (1:100) and mixed with lymphocytes, as described in Example 2.

FIGURE 3 is a graph showing that HIV infectivity was eliminated when various dilutions of high-titer viral stocks were incubated with 1.5% zinc acetate for 2 hours, as described in Example 3.

FIGURE 4 shows that HIV infectivity was eliminated or suppressed when high-titer HIV stocks were incubated with various concentrations of zinc acetate, as described in Example 3.

Signed and Sealed this

Twenty-second Day of October, 1996

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,482,053        Page 3 of 6
DATED : January 9, 1996
INVENTOR(S) : Patrick D. Kelly It is certified that error appears in the above-indentified patent and that said Letters Patent is hereby corrected as shown below:

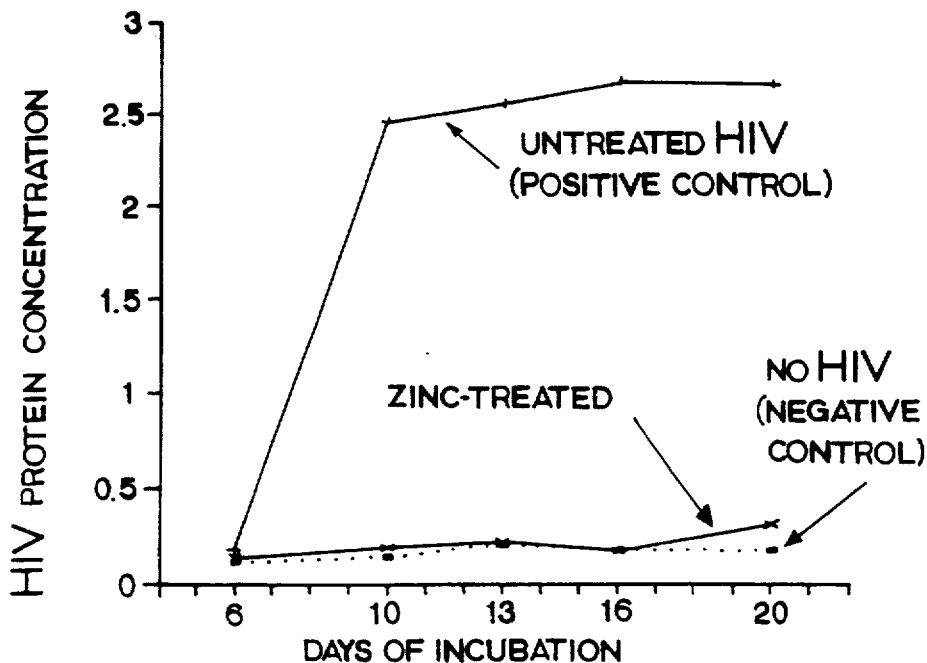

FIG.1.

UNITED STATES PATENT AND TRADEMARK OFFICE
CERTIFICATE OF CORRECTION

PATENT NO. : 5,482,053
DATED : January 9, 1996
INVENTOR(S) : Patrick D. Kelly

Page 4 of 6

It is certified that error appears in the above-indentified patent and that said Letters Patent is hereby corrected as shown below:

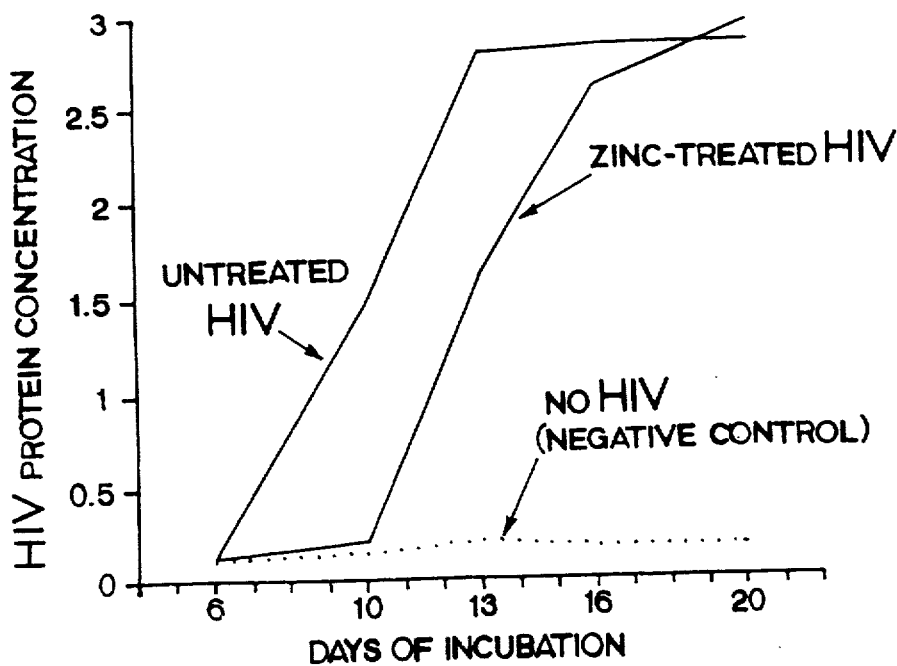

FIG.2.

UNITED STATES PATENT AND TRADEMARK OFFICE
CERTIFICATE OF CORRECTION

PATENT NO. : 5,482,053
DATED : January 9, 1996
INVENTOR(S) : Patrick D. Kelly

Page 5 of 6

It is certified that error appears in the above-indentified patent and that said Letters Patent is hereby corrected as shown below:

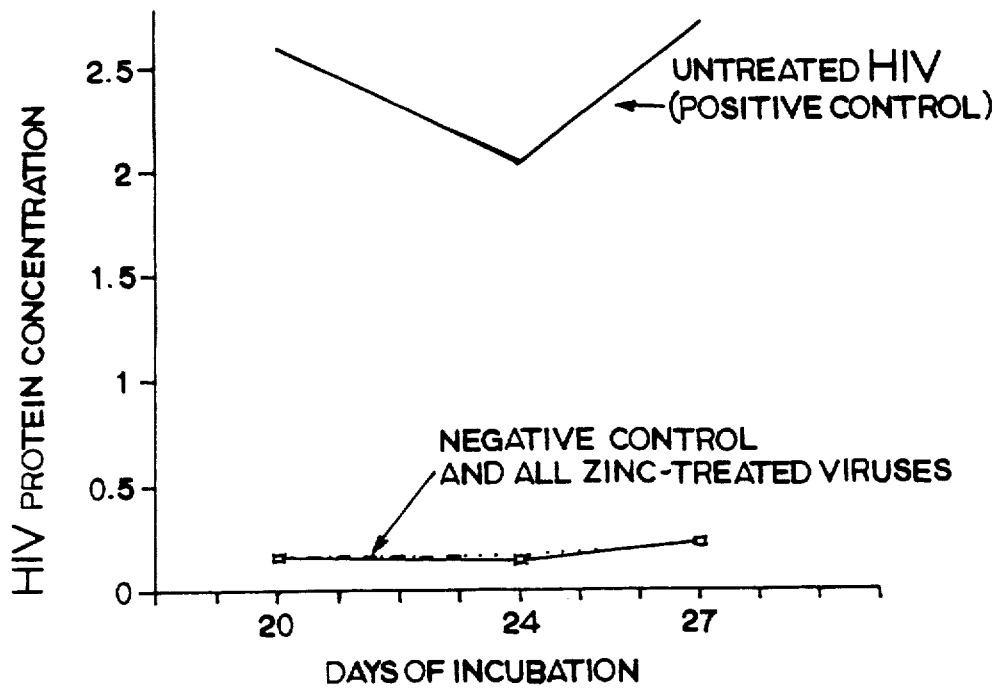

FIG.3.

UNITED STATES PATENT AND TRADEMARK OFFICE
CERTIFICATE OF CORRECTION

PATENT NO. : 5,482,053
DATED : January 9, 1996
INVENTOR(S) : Patrick D. Kelly

It is certified that error appears in the above-indentified patent and that said Letters Patent is hereby corrected as shown below:

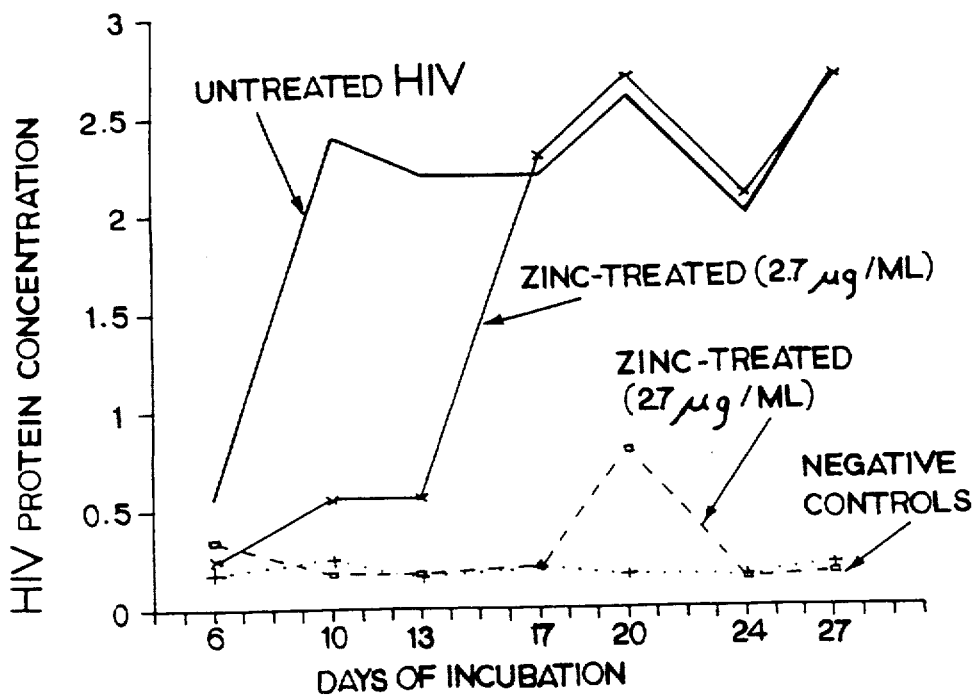

FIG.4.